United States Patent [19]
Maezaki et al.

[11] Patent Number: 4,911,708
[45] Date of Patent: Mar. 27, 1990

[54] SELF-SUPPORTABLE PARENTERAL BOTTLE OF SYNTHETIC RESIN

[75] Inventors: Yoshiki Maezaki, Tokushima; Tamotu Akamatu, Naruto, both of Japan

[73] Assignee: Otsuka Pharmaceutical Factory, Inc., Naruto, Japan

[21] Appl. No.: 192,099

[22] Filed: May 10, 1988

[30] Foreign Application Priority Data

May 18, 1987 [JP] Japan ............................ 62-74038[U]
Mar. 3, 1988 [JP] Japan ............................ 63-28840[U]

[51] Int. Cl.⁴ ............................................ A61B 19/00
[52] U.S. Cl. .............................. 604/408; 215/DIG. 3
[58] Field of Search ............... 604/408, 403, 404, 405, 604/406, 407, 905; 215/247, 346, 364, 1 C, DIG. 3

[56] References Cited

U.S. PATENT DOCUMENTS 3,215,299 9/1961 Coanda et al. .
3,325,031 6/1967 Singier ........................... 604/408 X
3,387,732 6/1968 Jellies .
3,509,879 5/1970 Bathish et al. ...................... 604/408
3,581,928 6/1971 St. Amand .
3,901,399 8/1975 McPhee .
4,013,187 3/1977 Betka .
4,100,953 7/1978 Miller .
4,282,980 8/1981 Winchell .

FOREIGN PATENT DOCUMENTS 5924041 8/1982 Japan .

*Primary Examiner*—John D. Yasko
*Attorney, Agent, or Firm*—Armstrong, Nikaido, Marmelstein, Kubovcik & Murray

[57] ABSTRACT

A proposal for reinforcing the bottom of a self-supportable parenteral bottle made of synthetic resin and having resting portions bulged downward from the bottom at opposite sides thereof, and a suspender flap downwardly projecting from and hingedly formed on a flat bottom portion between the resting portions on the center line of the bottom portion. The flat bottom portion has an endless ridge at its center, an upper flat bottom portion integral with and surrounded by the upper end of the ridge, and a lower flat bottom portion integral with and surrounding the lower end of the ridge, the lower flat bottom portion being gently sloped obliquely upward toward the center of the bottom, whereby the bottom of the bottle is precluded from bulging despite the thermal shrinkage resulting from molding or the rise of internal pressure due to sterilization by heating. The bottle is made self-supportable in an upright position reliably with good stability.

8 Claims, 3 Drawing Sheets

FIG.6-a

SELF-SUPPORTABLE PARENTERAL BOTTLE OF SYNTHETIC RESIN

TECHNICAL FIELD

The present invention relates to a self-supportable parenteral bottle of synthetic resin, and more particularly to improvements in the bottom structure of the bottle.

BACKGROUND ART

Self-supportable parenteral bottles of synthetic resin are known, and those of various constructions have already been proposed. Such parenteral bottles generally have resting portions bulged downward from the bottom at opposite sides thereof, and a suspender flap downwardly projecting from and hingedly formed on a flat bottom portion between the resting portions in alignment with the bottom center line. The resting portions to be seated and the suspender flap are molded simultaneously with the bottle body by a direct blow molding process. The suspender flap is held upright raised from the bottom when the parenteral bottle is suspended in an inverted position for use, but when the bottle is placed upright on a table or the like, the suspender flap is turned about a hinge at its base end to a folded position and accommodated in a space between the table surface and the bottle bottom to render the bottle self-supportable with good stability.

The bottom of the bottle is prone to deformation due to thermal shrinkage during the molding operation or due to a rise of the internal pressure when the bottle is sterilized by heating with a parenteral solution contained therein. Accordingly, the conventional parenteral bottle has the problem of failing to support itself stably when used in a standing position because the suspender flap can not be stowed completely in a folded position.

DISCLOSURE OF THE INVENTION

The main object of the invention is to overcome the problem of impaired self-supportability by reinforcing the bottom structure of such a bottle against deformation that could otherwise result from thermal shrinkage during the molding operation or from a rise of the internal pressure when the parenteral solution in the bottle is thermally sterilized.

Other features of the invention will become apparent from the following description.

The present invention provides a self-supportable parenteral bottle made of synthetic resin and having resting portions bulged downward from the bottom of the body of the bottle and positioned at opposite sides of the bottom, and a suspender flap downwardly projecting from and hingedly formed on a flat bottom portion between the resting portions in alignment with the center line of the flat bottom portion, the bottle being characterized in that the flat bottom portion has an endless ridge at its center, an upper flat bottom portion integral with and surrounded by the upper end of the ridge, and a lower flat bottom portion integral with and surrounding the lower end of the ridge, the lower flat bottom portion being gently sloped obliquely upward toward the center of the bottom of the bottle.

With the self-supportable parenteral bottle of the present invention, the upper flat bottom portion formed at the center of the bottom bulges downward, when the internal pressure of the bottle builds up during thermal sterilization, to distribute and absorb the pressure, thereby reducing the internal pressure acting on the lower flat bottom portion surrounding the upper bottom portion and diminishing the tendency for the entire bottom to buldge downward. The upward slope toward the center of the bottom given to the lower flat bottom portion also diminishes the tendency for the bottom to bulge downward owing to the thermal shrinkage involved in the molding operation, further giving the bottom increased resistance to the internal pressure. The ridge gives the flat bottom portion increased strength and enhanced resistance to the internal pressure, acting to lessen the tendency toward downward bulging.

The invention therefore obviates the likelihood that the bottom will bulge downward owing to thermal shrinkage during the molding operation or to a rise of internal pressure resulting from thermal sterilization. Accordingly, when the bottle is placed in an erect position, for example, on a table, a space of specified dimensions is formed between the table and the flat bottom portion by the protrusion of the resting portions. The suspender flap can be stowed in the space in a folded position free of any trouble, rendering the bottle self-supportable reliably with good stability.

BRIEF DESCRIPTION OF THE DRAWINGS

FIG. 6-*a* is an enlarged view in section of a hinge portion;

BEST MODE OF CARRYING OUT THE INVENTION

Figure 1:
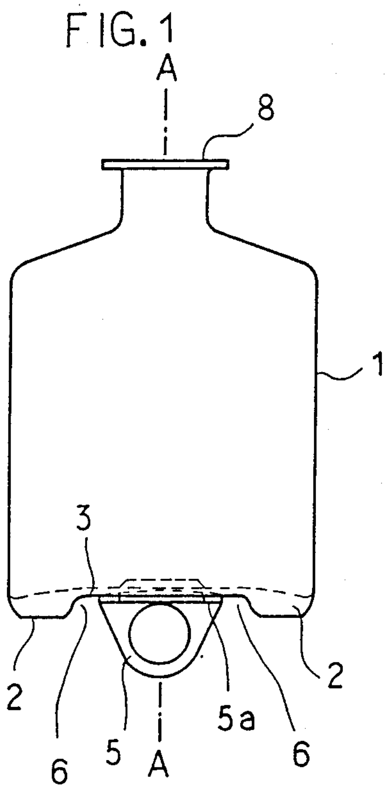
FIG. 1 is a front view showing a bottle body embodying the invention.
Figure 2:
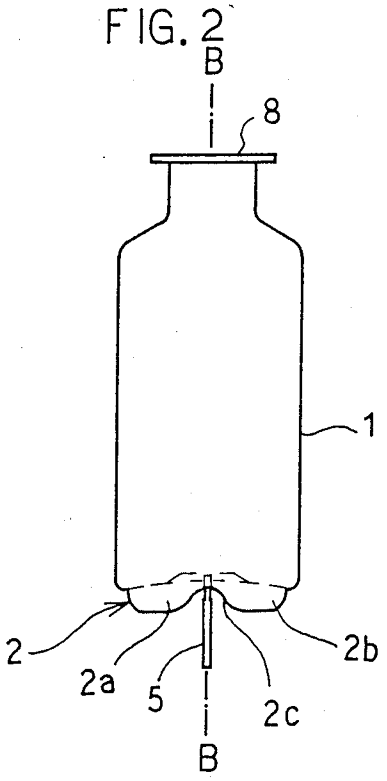
FIG. 2 is a side elevation of FIG. 1.
Figure 3:
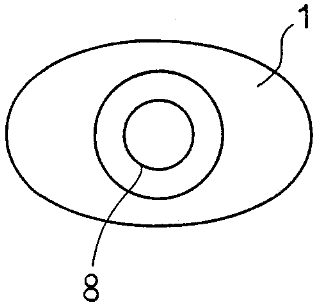
FIG. 3 is a plan view of FIG. 1.
Figure 4:
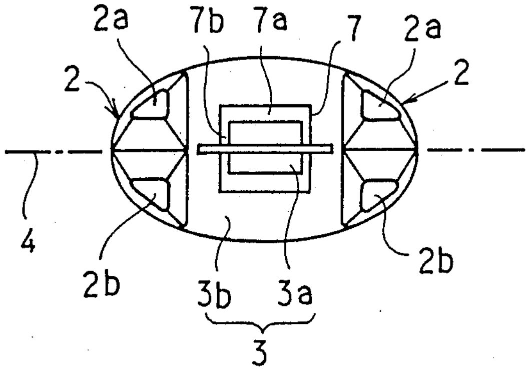
FIG. 4 is a bottom view of FIG. 1.
Figure 5:
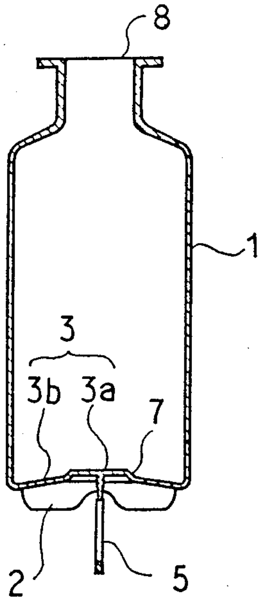
FIG. 5 is a view in section taken along the line A—A in FIG. 1.

An embodiment of the invention will be described below with reference to the accompanying drawings.

Like conventional self-supportable parenteral bottles, the bottle body 1 shown has a mouth 8 at its upper end, resting portions 2 bulged downward from the bottom of the bottle body at its opposite sides, and a suspender flap 5 downwardly projecting from a flat bottom portion 3 between the resting portions 2, 2 and aligned with the center line (parting line) 4 of the flat bottom portion 3. The resting portions 2 and the suspender flap 5 are molded integrally with the body 1 at the same time by the direct blow molding process.

The bottle body 1 is molded from a flexible synthetic resin material such as polyethylene, polypropylene, polyvinyl chloride, ethylene vinyl alcohol or ethylene-vinyl acetate copolymer according to the conventional practice.

Figure 7:
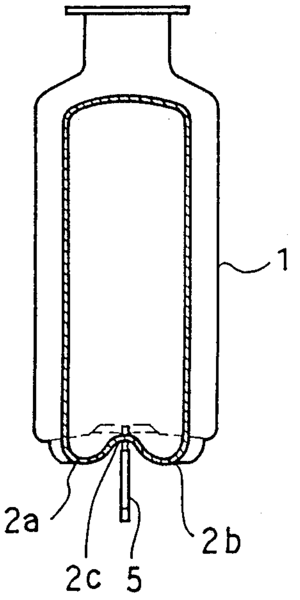
FIG. 7 is a view in section taken along the line C—C in FIG. 6.
Figure 7:
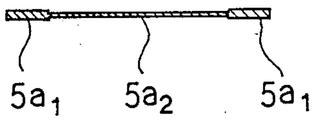

When required, the resting portion 2 at each side of the bottom of the body 1 can be divided into two portions, i.e. a front portion **2*a* and a rear portion 2*b*, at opposite sides of a furrow 2***c* on the center line 4 (see FIG. 7).

Figure 6:
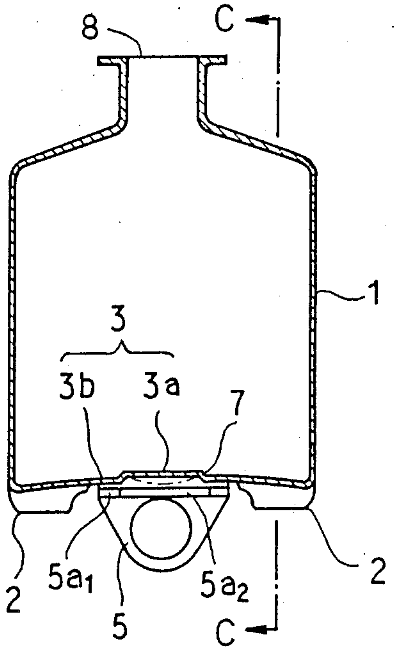
FIG. 6 is a view in section taken along the line B—B in FIG. 2.

The suspender flap 5 is movable to an upright position or to a folded position, as supported by a baseend hinge portion 5*a* (see FIG. 1). When the bottle body 1 is used in an inverted position, the flap 5 is raised upright to serve as a suspender, whereas when the body 1 is used in an erect position, the flap 5 is folded over the flat bottom portion 3 so as not to impair the self-supportability of the bottle body 1. Insofar as only the stability of the bottle body 1 in its standing position is concerned, the hinge portion 5*a* preferably has the smallest possible thickness, but if it is too thin, there is the undesirable likelihood that tee flap 5 will separate off during molding or deform owing to thermal shrinkage. To obviate this problem, the hinge portion 5*a* has opposite end parts $5a_1$, 5*a*1 of a relatively large thickness (e.g. 0.25 to 0.45 mm) and a middle part $5a_2$ of a relatively small thickness (e.g. about 0.2 mm) as seen in FIG. 6 and FIG. 6-*a*. Spaces are provided at opposite ends of the suspender flap 5 outside thereof (see FIG. 1) for use in removing fins and have such a width as to permit a fin removing blade to enter the space.

The bottom structure of the parenteral bottle of the invention is characterized in that the flat bottom portion 3 has an endless ridge 7 at its center, an upper flat bottom portion 3*a* integral with and surrounded by the upper end of the ridge 7, and a lower flat bottom portion 3*b* integral with and surrounding the lower end of the ridge 7, the lower flat bottom portion 3*b* being gently sloped obliquely upward toward the center of the bottom of the bottle.

When seen from above, the ridge 7 is rectangular in shape as illustrated. The ridge 7 has such a height and angle as to make the molding dies openable free of any trouble. For example, ween the bottle has a capacity of 100 to 200 ml, it is suitable that the ridge be about 1 to about 5 mm in height and have, with respect to the lower flat bottom portion 3*b*, a small angle of about 10 to about 50 degrees at its sides *7a, 7a* transverse to the die opening direction and a large angle of about 30 to about 80 degrees at the other sides *7b, 7b* thereof along the die opening direction.

The central upper flat bottom portion 3*a* surrounded by the ridge 7 serves to distribute and absorb the rise of internal pressure resulting from thermal sterilization and occupies preferably at least 10% of the entire area of the bottom of the bottle. Usually, the area of the portion 3*a* ranges from 10 to 50% of the entire bottom area.

The ridge 7, i.e. the upper flat bottom portion 3*a*, which is rectangular when seen from above as illustrated, may alternatively be in the form of a circle (inclusive of ellipse and elongated circle) or polygon or otherwise shaped as desired. Especially it is suitable that the portion 3*a* resemble the bottom of the bottle in shape as viewed from above.

The upward slope given to the lower flat bottom portion 3*b* surrounding the ridge 7 serves to obviate the deformation due to thermal shrinkage involved in molding and to afford increased resistance to the increase of internal pressure due to thermal sterilization. Although it is desirable that the slope be as great as possible, too great a slope will cause trouble in opening the dies, so that the slope is suitably 15 degrees or less. The illustrated bottom portion 3*b* has a slope of about 3 degrees along the major axis and about 5 degrees along the minor axis.

With the bottom structure of the present invention, the upper flat bottom portion 3*a* at the center bulges as indicated in a chain line in FIG. 6 when the internal pressure of the bottle builds up during thermal sterilization to absorb and distribute the pressure, thereby reducing the internal pressure acting on the lower flat bottom portion 3*b* surrounding the portion 3*a*. The upward slope given to the lower flat bottom portion 3*b* diminishes the tendency for the bottom to bulge downward owing to the thermal shrinkage involved in molding, further giving improved resistance to the internal pressure. The ridge 7 affords increased strength to the flat bottom portions 3*a*, 3*b* and acts to lessen the tendency for these portions to bulge downward. The present invention therefor eliminates the likelihood that the bottom will bulge downward, despite the thermal shrinkage during molding or the rise of internal pressure due to thermal sterilization, thus providing a product which is self-supportable with good stability.

Figure 8:
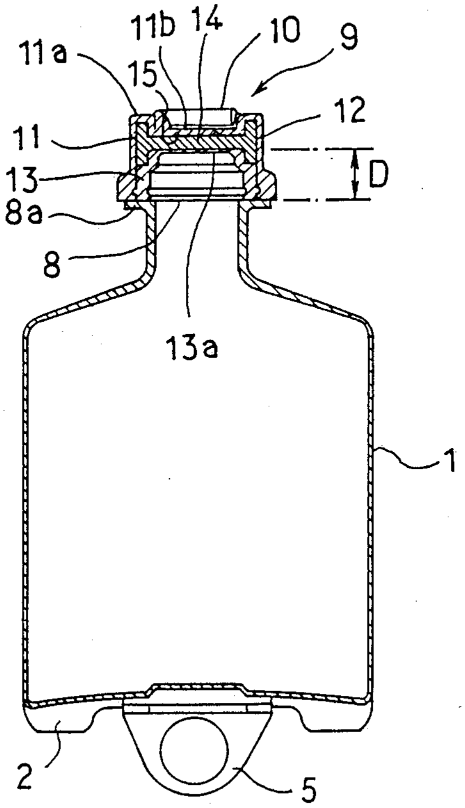
FIG. 8 is a view in vertical section showing the bottle body provided with a closure.
Figure 9:
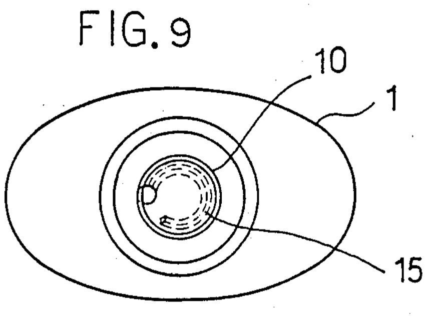
FIG. 9 is a plan view of the same.

With reference to FIG. 8, the mouth 8 of the bottle body 1 at its upper end is provided with a closure 9. As illustrated, the closure 9 has a pull ring 10, by which a closure portion is removable conveniently by a pull. A preferred example of closure 9 having the pull ring 10 will be described below with reference to FIG. 8.

The closure 9 shown in FIG. 8 comprises a plastic cap 11 having the pull ring 10, a caplike plastic plug 13 closing the lower end of the cap 11 with a clearance 12 of H-shaped section formed between the cap 11 and the plug 13, and a rubber stopper 14 of H-shaped section fitted in the clearance 12 in intimate contact with the cap and the plug.

To form the clearance 12 of H-shaped section between the plug 13 and the cap 11, the cap 11 has an annular upward projection 11*a* along the outer periphery of its top, and a flat top central portion 11*b* surrounded by the annular projection 11*a*. The central portion 11*b* is provided with the pull ring 10 for suitably removing the portion 11*b* along a score 15 to expose the top surface of the rubber stopper 14.

To form the clearance 12 of H-shaped section between the cap 11 and the plug 13, the plug 13 closing the lower end of the cap 11 has a smaller outside diameter at its upper portion than at its lower portion.

The lower ends of the cap 11 and the plug 13 are flush with each other to provide a face fused to an outer flange 8*a* around the mouth portion 8 of the bottle body 1. The fused face can be enlarged, for example, by giving an increased wall thickness to the lower portion of the cap 11 as illustrated.

While the cap 11 and the plug 13 are made of a material which is not limited specifically insofar as these members can be bonded by fusion to the bottle body 1, they are usually made of the same material as the bottle body 1, such as polyethylene, polypropylene or like flexible plastic material.

The rubber stopper 14 tightly fitted in the clearance 12 between the cap 11 and the plug 13 is prevented from slipping off the cap 11 when the bottle is opened for use because the stopper is H-shaped in section. The rubber stopper 14 is made of the same material as conventionally used for parenteral bottles.

When the closure 9 is attached to the flange 8*a* at the upper end of the bottle body 1 by fusing the lower ends of the cap 11 and the plug 13, a film portion 13*a* at the upper end of the plug 13 is likely to be softened and deformed by the heat of fusing operation, if the distance D between the fused face and the film portion 13*a* shown in FIG. 8 is small. The upper-end film portion 13*a* generally has a small thickness for a needle passed through the rubber stopper 14 to penetrate the film portion for withdrawing the parenteral solution, so that the film portion 13 is likely to develop a pinhole or crack when thermally deformed. However, the likelihood of developing the pinhole or crack can be obviated by setting the distance D to about 10 mm to preclude occurrence of rejects. Although a shield plate is conventionally used for shielding the closure and therefore the film portion 13*a* from the heater to eliminate the thermal influence on the film portion 13*a*, the distance D of about 10 mm, when provided, obviates the need to use the shield plate, consequently ensuring a quick and efficient fusing operation and achieving improved productivity.

We claim:

1. A self-supportable parenteral bottle made of synthetic resin and having resting portions bulged downward from the bottom of the body of the bottle and positioned at opposite sides of the bottom, and a suspender flap downwardly projecting from and hingedly formed on a flat bottom portion between the resting portions in alignment with the center line of the flat bottom portion, the bottle being characterized in that the flat bottom portion has an endless ridge around its center, an upper flat bottom portion integral with and surrounded by the upper end of the ridge, and a lower flat bottom portion integral with and surrounding the lower end of the ridge, the lower flat bottom portion being gently sloped obliquely upward toward the center of the bottom of the bottle.

2. A bottle as define in claim 1 wherein the upper flat bottom portion surrounded by the ridge occupies 10 to 50% of the entire area of the bottom of the bottle.

3. A bottle as defined in claim 1 wherein the ridge is 1 to 5 mm in height and has, with respect to the lower flat bottom portion, an angle of 10 to 50 degrees at its sides transverse to the die opening direction and an angle of 30 to 80 degrees at its sides along the die opening direction.

4. A bottle as defined in claim 1 wherein the lower flat bottom portion is upwardly sloped at an angle of 15 degrees or less.

5. A bottle as defined in claim 1 wherein the mouth of the bottle body comprises a neck portion at its upper end which is provided with a closure having a pull ring.

6. A bottle as defined in claim 5 wherein the closure comprises a plastic cap having the pull ring, a caplike plastic plug closing the lower en of the cap with a clearance of H-shaped section formed between the cap and the plug, and a rubber stopper of H-shaped section fitted in the clearance in intimate contact with the cap and the plug.

7. A bottle as defined in claim 6 wherein the closure is fused at its lower end face to the upper end of the bottle body, and the plug has a film portion at its upper end, the distance between the fused end face and the film portion being about 10 mm.

8. A self-supportable parenteral bottle made of synthetic resin and having resting portions bulged downward from the bottom of the body of the bottle and positioned at the outer periphery of the bottle bottom, and a suspender flap means downwardly projecting from and hingedly connected to the bottle bottom, wherein said bottle bottom comprises a first region inward of said resting portions gently sloping obliquely upward and inward toward the center of said bottle bottom, region having a great upward slope than the first region, said second region inwardly terminating in a third, substantially flat region comprising the central portion of said bottle bottom.

* * * * *